US010076631B2

United States Patent
Liu (10) Patent No.: US 10,076,631 B2
(45) Date of Patent: Sep. 18, 2018

(54) MEDICAL CABIN SYSTEM AND METHOD FOR USING THE SAME

(71) Applicant: OUR NEW MEDICAL TECHNOLOGIES, Shenzhen (CN)

(72) Inventor: Haifeng Liu, Xi'an (CN)

(73) Assignee: OUR NEW MEDICAL TECHNOLOGIES, Shenzhen (CN)

( * ) Notice: Subject to any disclaimer, the term of this patent is extended or adjusted under 35 U.S.C. 154(b) by 398 days.

(21) Appl. No.: 14/417,186

(22) PCT Filed: Feb. 6, 2013

(86) PCT No.: PCT/CN2013/071430
§ 371 (c)(1),
(2) Date: Jan. 26, 2015

(87) PCT Pub. No.: WO2014/121458
PCT Pub. Date: Aug. 14, 2014

(65) Prior Publication Data
US 2015/0328432 A1    Nov. 19, 2015

(51) Int. Cl.
*A61M 21/02* (2006.01)
*A61M 21/00* (2006.01)
(Continued)

(52) U.S. Cl.
CPC .............. *A61M 21/02* (2013.01); *A61G 10/00* (2013.01); *A61M 21/0094* (2013.01);
(Continued)

(58) Field of Classification Search
CPC .............. A61M 21/02; A61M 21/0094; A61M 2021/0044; A61M 2205/505;
(Continued)

(56) References Cited

U.S. PATENT DOCUMENTS 6,798,201 B2 * 9/2004 Kuth ..................... A61B 5/0046
324/317
2003/0197593 A1 * 10/2003 Siegel ................ G07C 9/00087
340/5.52
(Continued)

FOREIGN PATENT DOCUMENTS

CN          1886170       12/2006
CN       101313633 A     11/2008
(Continued)

*Primary Examiner* — Kaylee Wilson
(74) *Attorney, Agent, or Firm* — Hemisphere Law, PLLC; Zhigang Ma (57) ABSTRACT

A medical cabin system comprises a safety protection structure, an identification structure, an environment simulation structure, a radiotherapy isolation structure, and one or more other independent walls. The safety protection structure is disposed on an entrance of the medical cabin system. The identification structure is disposed on a medical equipment of the medical cabin system or in an enclosed space defined by a stereo location region of the medical cabin system. The environment simulation structure is disposed on a top portion and at least one side wall of the medical cabin system. The radiotherapy isolation structure isolates the stereo location region from a radiotherapy region of the medical cabin system. The independent walls define at least one enclosed space with the radiotherapy isolation structure.

10 Claims, 11 Drawing Sheets

(51) Int. Cl.
*A61G 10/00* (2006.01)
*A61N 5/10* (2006.01)
*A61N 5/00* (2006.01)
*G21F 7/00* (2006.01)
*G21F 3/00* (2006.01)

(52) U.S. Cl.
CPC ............... *A61M 2021/005* (2013.01); *A61M 2021/0027* (2013.01); *A61M 2021/0044* (2013.01); *A61M 2205/051* (2013.01); *A61M 2205/505* (2013.01); *A61M 2205/6009* (2013.01); *A61M 2205/609* (2013.01); *A61M 2205/6054* (2013.01); *A61N 5/00* (2013.01); *A61N 5/1048* (2013.01); *A61N 2005/1074* (2013.01); *A61N 2005/1094* (2013.01); *G21F 3/00* (2013.01); *G21F 7/00* (2013.01)

(58) Field of Classification Search
CPC ...... A61M 2205/051; A61M 2021/005; A61M 2205/6054; A61G 10/00; G21F 3/00; G21F 7/00; A61N 2005/1094; A61N 2005/1074; A61N 5/1048; A61B 5/0046
See application file for complete search history.

(56) References Cited

U.S. PATENT DOCUMENTS

| | | | | |
|---|---|---|---|---|
| 2007/0176920 | A1* | 8/2007 | Raijmakers | A61M 21/00 345/418 |
| 2008/0105387 | A1* | 5/2008 | Coleman | E05D 15/0652 160/194 |
| 2008/0171935 | A1* | 7/2008 | McKnight | A61B 5/702 600/415 |
| 2010/0217111 | A1 | 8/2010 | Dietz | |

FOREIGN PATENT DOCUMENTS

| | | |
|---|---|---|
| CN | 202042069 A | 11/2011 |
| CN | 102779225 Y | 11/2012 |
| CN | 203226833 E | 10/2013 |
| HU | 222163 A | 7/2001 |

* cited by examiner

FIG. 1

PRIOR ART

MEDICAL CABIN SYSTEM AND METHOD FOR USING THE SAME

TECHNICAL FIELD

The present invention relates to a medical cabin system, and in particular, to a patient experience-orientated medical cabin system and a method using the same.

BACKGROUND

Figure 1:
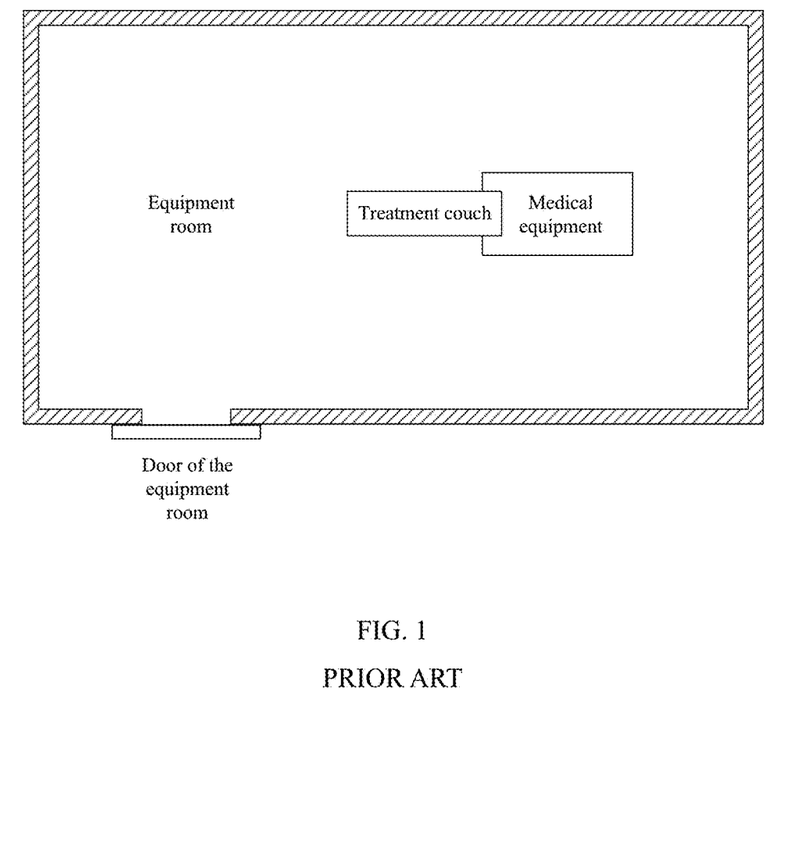
FIG. 1 is a schematic structural diagram of a traditional medical cabin system.

In the field of radiotherapy, medical equipment (especially large medical equipment) is used to conduct imaging diagnosis or radiotherapy on patients, while being enclosed in a space/room/cabin. FIG. 1 is a schematic structural diagram of a traditional medical cabin system. As illustrated in FIG. 1, the equipment is independently installed in an equipment room. During the diagnosis, the patient opens the door of the equipment room and goes to lie on the couch of the medical equipment. Then, the patient is delivered to a predetermined position of the medical equipment by the treatment couch for imaging diagnosis or radiotherapy. In the whole process, the patient will always feel passive and tense, causing an environment of repression during the diagnosis or the treatment. During the treatment, if disturbance (for example, noise of the equipment and dialogs between doctors and patients outside the equipment room made by) caused by ambient factors is present, psychological pressure may be caused to of treatment possibly, which may lead to a poor treatment effect.

SUMMARY

An embodiment of the present invention provides a medical cabin system used for a radiotherapy system. The medical cabin system comprises: a safety protection structure, disposed on an entrance of the medical cabin system; an identification structure, disposed on a medical equipment of the medical cabin system or in an enclosed space defined by a stereo location region of the medical cabin system; an environment simulation structure, disposed on a top portion and at least one side wall of the medical cabin system; a radiotherapy isolation structure, the radiotherapy isolation structure isolates the stereo location region from a radiotherapy region of the medical cabin system; and one or more other independent walls defining at least one enclosed space with the radiotherapy isolation structure.

An embodiment of the present invention provides a method for using a medical cabin system which is used for a radiotherapy system, the method comprises: entering the medical cabin system via a safety protection structure, the safety protection structure being disposed on an entrance of the medical cabin system; performing identification via an identification structure and starting radiotherapy if the identification is successful, the identification structure being disposed on medical equipment of the medical cabin system or an enclosed space defined by a stereo location region of the medical cabin system; simulating an environment of the medical cabin system via an environment simulation structure, the environment simulation structure being disposed on a top portion and at least one side wall of the medical cabin system; and defining independent spaces by enclosing the stereo location region and a radiotherapy region respectively via a radiotherapy isolation structure, wherein the radiotherapy isolation structure isolates the stereo location region from the radiotherapy region, and the medical cabin system further comprises one or more other independent walls defining at least one enclosed space with the radiotherapy isolation structure.

The medical cabin system and the method for using the medical cabin system according to the embodiments of the present invention are patient experience-orientated during the whole diagnosis and treatment, and bring the patient into virtual experience of staying at other environments (for example, in a space medical cabin) during the treatment, thereby improving the patient's trust on high-tech medical equipment, enhancing confidence for the treatment and relieving nervousness and anxiety of the patient, and hence improving treatment comfort and diagnosis effect for the patient.

DETAILED DESCRIPTION

The technical solutions of the present invention are further described in detail with reference to attached drawings and specific embodiments. Obviously, the embodiments described herein are merely exemplary ones, but are not all the embodiments. Based on the embodiments of the present invention, all other embodiments derived by persons of ordinary skill in the art without any creative efforts shall fall within the protection scope of the present invention.

Figure 2:
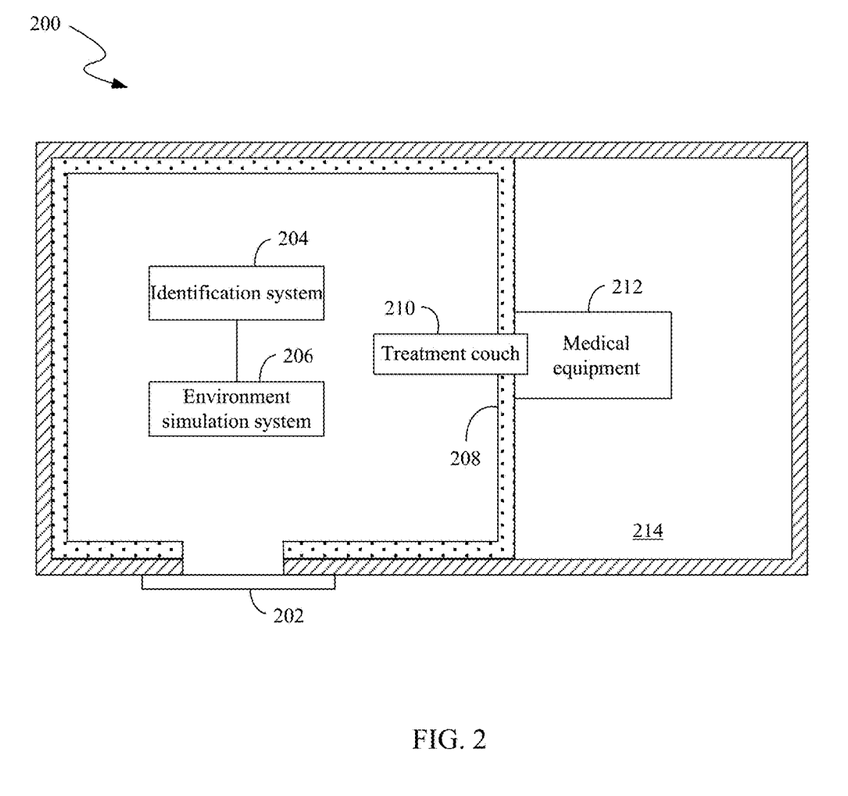
FIG. 2 is a schematic structural diagram of a medical cabin system according to an embodiment of the present invention.

FIG. 2 is a schematic structural diagram of a medical cabin system according to an embodiment of the present invention. As illustrated in FIG. 2, the medical cabin system 200 comprises: a safety protection structure 202, an identification structure 204, an environment simulation structure 206, a radiotherapy isolation structure 208, a treatment couch 210, a medical equipment 212, and an equipment room 214. The safety protection structure 202 may be disposed on an entrance of the medical cabin system 200, and comprises an equipment room door. The identification structure 204 may be disposed on a medical equipment of the medical cabin system or in an enclosed space defined by a stereo location region of the medical cabin system 200. The environment simulation structure 206 may be disposed on a top portion and a side wall of the medical cabin system 200. The radiotherapy isolation structure 208 may be a vertical wall that isolates the stereo location region from the radiotherapy region of the medical cabin system 200, wherein the medical cabin system 200 may further comprise one or more other independent walls defining an enclosed space with the vertical wall. It should be noted that the structure illustrated in this embodiment is merely an example, but not a limitation, and a person skilled in the art may understand and apply another suitable structure.

Figure 3:
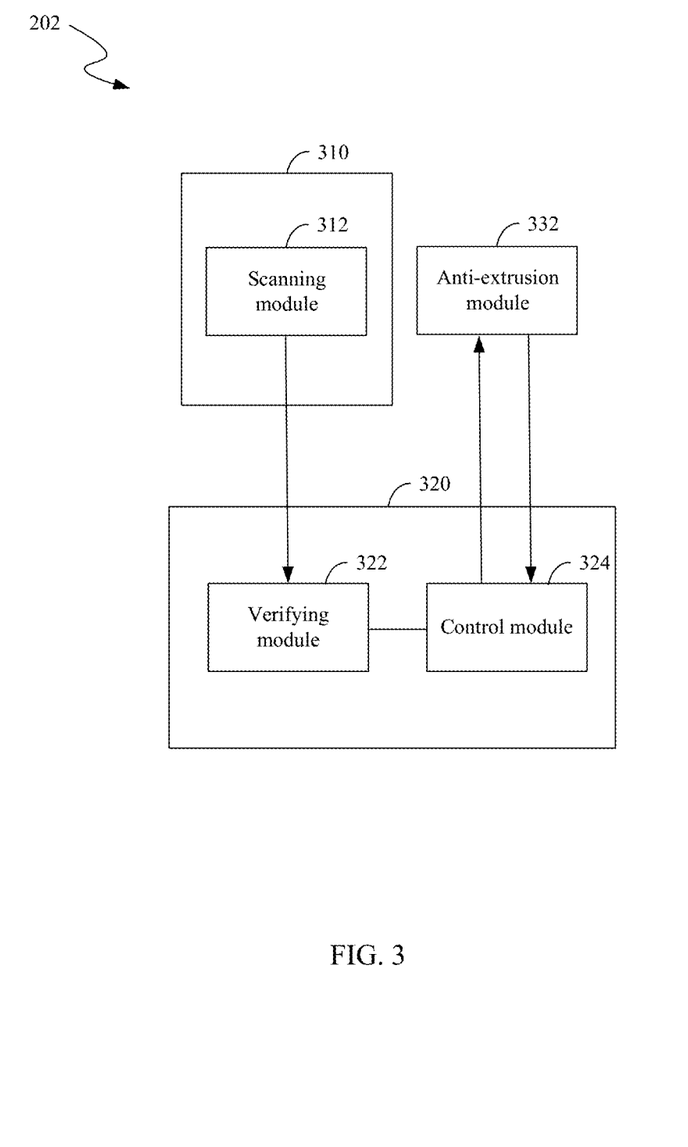
FIG. 3 is a schematic structural diagram of a safety protection structure according to an embodiment of the present invention.

The safety protection structure 202 is specifically described with reference to FIG. 3. The safety protection structure 202 comprises an installation panel 310, a scanning module 312, a verifying module 322, a control module 324, and an anti-extrusion module 332. The scanning module 312 is disposed on the installation panel 310, and is coupled to a treatment controlling computer 320 of the radiotherapy system (for example, they are coupled via cable). The verifying module 322 and the control module 324 are executed by the treatment controlling computer 320. The control module 324 is coupled to the verifying module 322, a driving unit (e.g. motor) of the shielding door, and the anti-extrusion module 332.

In the treatment process, an operator (for example, a patient) takes to-be-scanned identity characteristics (for example, fingerprint) close to the scanning module 312 (for example, an electronic lock of fingerprint), and the scanning module 312 scans the identity characteristics of the operator and sends a scanning result to the verifying module 322. The verifying module 322 extracts prestored identity characteristic information of the patient and performs matching-based verification on the prestored identity characteristic information and the scanning result, and sends a verification result to a the control module 324. The control module 324 controls open and close movements of a shielding door at the entrance according to the verification result by using the driving unit (not illustrated in the drawing) of the shielding door.

In one embodiment, the control module 324 is a shielding door smart control module, and is installed in the treatment controlling computer. If the scanning result sent by the scanning module 312 matches with the prestored characteristic information of the patient extracted by the verifying module 322 (that is, the verification result is true), the control module 324 controls the shielding door to open. After the shielding door is opened, it will be automatically closed in case of timeout, and meanwhile the anti-extrusion function is enabled. After the shielding door is closed, if the shielding door is desired to be opened from inside of the equipment room, a button disposed on the inner wall for manual opening the shielding door can be pressed. If the button is pressed, the shielding door is opened; if the button is released during the opening process, the shielding door immediately stops moving and remains at its position at that moment; if the button is pressed again, the shielding door continues opening, and so on until the shielding door is fully opened. If the duration when the shielding door remains at any position exceeds a predetermined value, the shielding door starts to close automatically, and the anti-extrusion function is enabled (that is, the anti-extrusion module 332 is activated). On the contrary, if the scanning result sent by the scanning module 312 does not match with the prestored characteristic information of the patient extracted by the verifying module 322 (that is, the verification result is false), the control module 324 controls the shielding door to close. In this case, the operator may perform the scanning operation again.

Specifically, the installation panel 310 forms a fixing bracket on which the scanning module 312 is disposed, and is disposed on an outer wall face of the equipment room on the side of the shielding door. The scanning module 312 may be coupled to the treatment controlling computer 320 via cable, and is in data communication with the verifying module 322. The driving unit (not illustrated in the drawing) of the shielding door is coupled to the control module 324 via cable, and receives a control instruction sent by the control module 324. The anti-extrusion 332 is disposed on one side of the shielding door, which may be somewhat modified to make the appearance thereof to be integral with the shielding door. The anti-extrusion module 332 may be coupled to the control module 324 via cable. When the anti-extrusion module 332 is subjected to external resistance of a specific size, the anti-extrusion module 332 sends a signal to the control module 324 to control the shielding door to stop moving and start running a program for opening the shielding door, until the shielding door is fully opened.

It should be noted that the identity characteristic information scanned by the scanning module 312 may be fingerprint, palm print, retina, and face, which is not limited in the present invention. In addition, although in the embodiment illustrated in FIG. 3, only one safety protection structure disposed on a door (that is, the outer wall of the door of the equipment room), the description of FIG. 3 and the number of doors are for illustration purpose only, rather than limitation. On the contrary, a person skilled in the art may understand that the safety protection structure 202 is not merely involved in the radiotherapy equipment room, but also comprises the electronic safety protection structure embedded in the secondary treatment equipment (for example, the medical cabin) room in the radiotherapy equipment room. If necessary, the safety protection structure 202 may be disposed on two or more doors, and the installation position may not be limited to the outer wall of the door of the equipment room, but for example may also be disposed on the outer wall of the door of the medical cabin.

Advantageously, the safety protection structure 202 controls open and close movements of the shielding door by smartly identifying the current patient's identity, according to such identity characteristic information as the fingerprint, palm print, retina and face, thereby preventing the patient's identity from being confused. In addition, during the treatment, unless a higher level of permission is given, the shielding door cannot be opened from the outside, thereby preventing the occurrence of misoperation. Further, the anti-extrusion function is enabled when the door is closed, thereby preventing exceptional extrusion of the electrical control system causing incidents of deaths or injuries.

Figure 4:
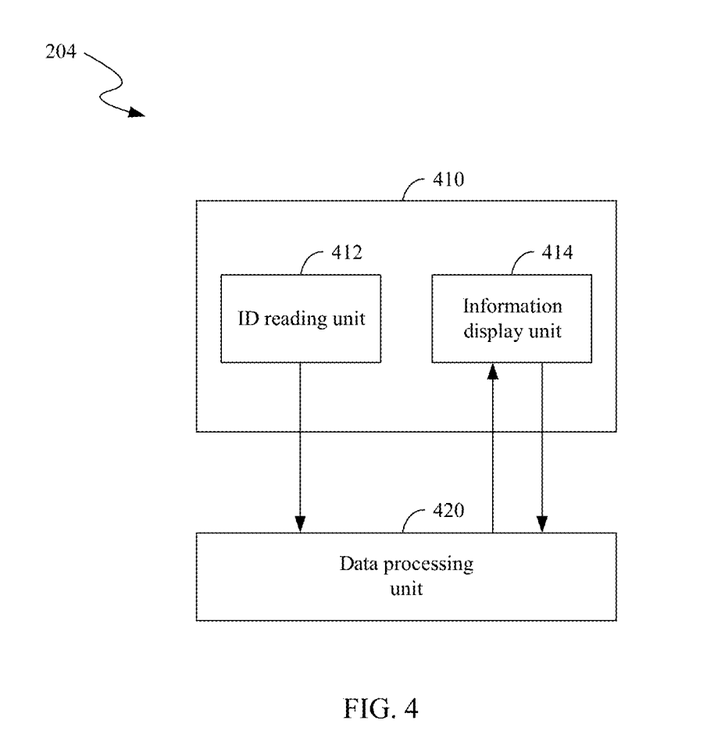
FIG. 4 is a schematic structural diagram of an identification structure according to an embodiment of the present invention.
Figure 5:
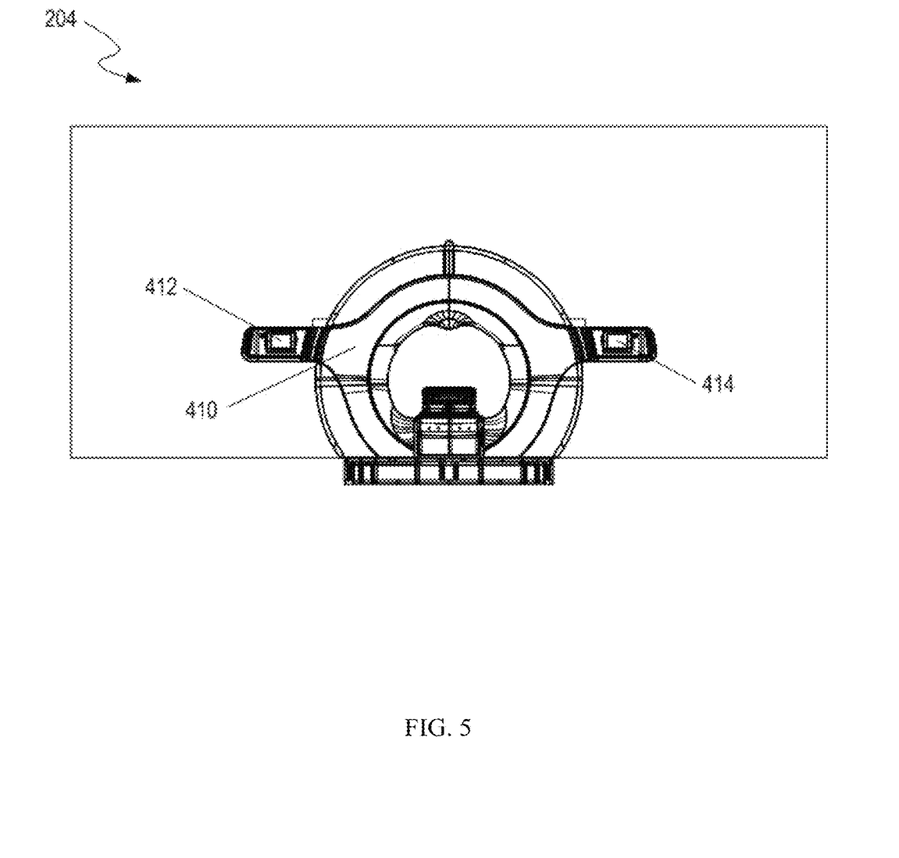
FIG. 5 is a front view of the identification structure according to an embodiment of the present invention.

The identification structure 204 is described with reference to FIG. 4. As illustrated in FIG. 1, the identification structure 204 comprises an installation panel 410 and a data processing unit 402. With reference to the front view given in FIG. 4, the installation panel 410 may be disposed on radiotherapy equipment or any appropriate visual region of the enclosed space defined by a stereo location region of the medical cabin system. An ID reading unit 412 (for example, an ID card reader) and an information display unit 414 (for example, a touch operable display) may be disposed on the installation panel 410 respectively. The ID reading unit 412 and the information display unit 414 are both coupled to the data processing unit 420. For example, these two units may be coupled to each other via cable.

During the treatment, at first, a card swiping operation needs to be performed on the ID reading unit 412. The ID reading unit 412 reads electronic information such as barcode information from an ID card of the patient, and sends the electronic information to the data processing unit 420. The data processing unit 402 conducts a search in a local database according to the electronic information sent by the ID reading unit 412, and outputs corresponding information of a search result to the information display unit 414 for display. Hence, the information display unit 414 in real time displays the information sent by the data processing unit 420 on the screen thereof, and provides a man-machine interactive interface for operator's operations, and the operation result will be sent back synchronously to the display interface of the data processing unit 420.

In one embodiment, the data processing unit 420 is disposed on the treatment controlling computer. If the data processing unit 420 detects that the barcode information sent by the ID reading unit 412 matches with the data in the local database (that is, the search result is true), the information display unit 414 displays pictures and treatment parameters of the current patient to be treated. If the pictures and treatment parameters are correct, the operator (for example, the patient) may click the confirm function key on the information display unit 414 to perform an operation for a final confirmation of the identity and treatment parameters of the patient. Then the data processing unit may deliver the treatment parameter to an electrical control system in a lower computer according to the confirmation information sent by the information display unit 414, and starts radiotherapy for the patient. On the contrary, if the data processing unit 420 detects that the barcode information sent by the ID reading unit 412 does not match with the data in the local database (that is, the search result is false), the information display unit 414 displays information such as "error", "no treatment data available" or "treatment on the patient is finished", to prompt error information to the operator. In this case, the operator may re-confirm the correctness of the ID card, thereby preventing occurrence of the medical incidents.

Specifically, the identification structure 204 comprises the installation panel 410, the ID reading unit 142, the information display unit 414, and the data processing unit 420. The installation panel 410 may be disposed on radiotherapy equipment or any appropriate visual region of the equipment room, so as to perform the card swiping operation of the ID reading unit 412 and information reading of the information display unit 414. The installation panel 410 forms a fixing bracket where the ID reading unit 412 and the information display unit 414 are disposed. The data processing unit 420 may be disposed in the treatment controlling computer. The data processing unit 420 may be coupled to the ID reading unit 412 via cable, and the data processing unit 420 may be coupled to the information display unit 414 via cable too.

It should be noted that the ID reading unit 412 may employ such techniques as magnetic card, chip card, one-dimension code or two-dimension code etc. The information displaying unit 414 may be a touch screen or non-touch screen, which may display information and in real time communicate and interact with the data processing unit 420 in the treatment controlling computer. The treatment controlling computer may be disposed in any operable range during the radiotherapy process.

Advantageously, the identification structure 204 smartly identifies the identity of a patient by using such a technique as barcode, allowing the patient actively participate in the whole process of check and delivery of the treatment parameters. This prevents judgment mistakes due to subjective factors and thus reduces the occurrence of medical incidents. In addition, introduction of smart high-tech techniques improves the high-tech environment of the radiotherapy system.

Figure 6:
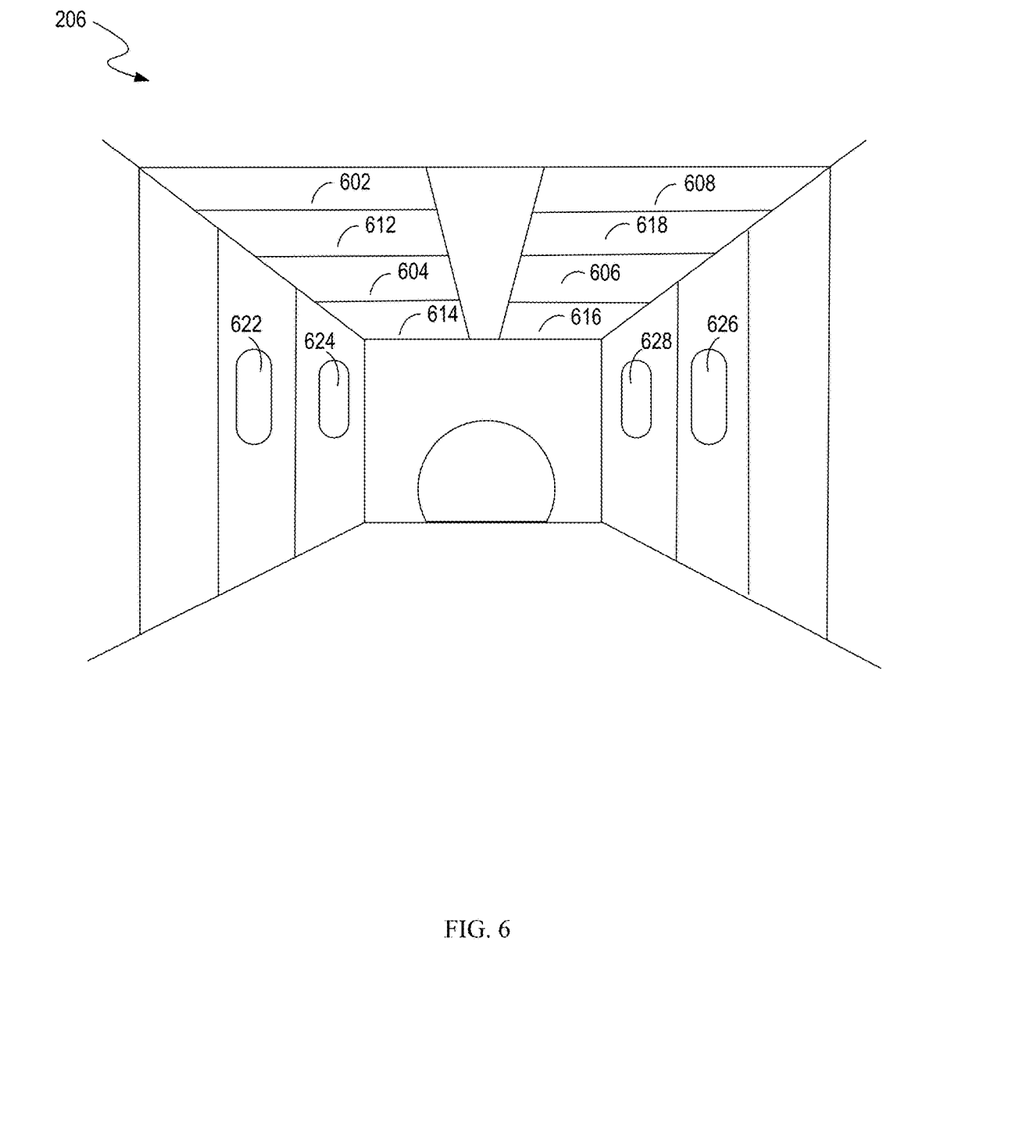
FIG. 6 is a schematic structural diagram of an environment simulation structure according to an embodiment of the present invention.

The environment simulation structure 206 is described with reference to FIG. 6. It should be noted that although the embodiment illustrated in FIG. 6 gives the specific installation position (for example, the top portion or side wall) of a illumination device and a display device, the description in the embodiment illustrated in FIG. 6 is for illustration purpose only, rather than limitation. On the contrary, a person skilled in the art may understand that the illumination device, the display device and the speaker device may be disposed at any suitable position, for cooperatively achieving a vivid effect of the simulation. As illustrated in FIG. 6, illumination devices 602, 604, 606, and 608 may be disposed on the top portion (for example, roof or ceiling of the equipment room) of the environment simulation structure 206. Display devices 612, 614, 616, and 618 may be disposed on the top portion of the environment simulation structure 206. In addition, display devices 622, 624, 626, and 628 may be disposed on the side wall of the environment simulation structure 206.

Figure 7:
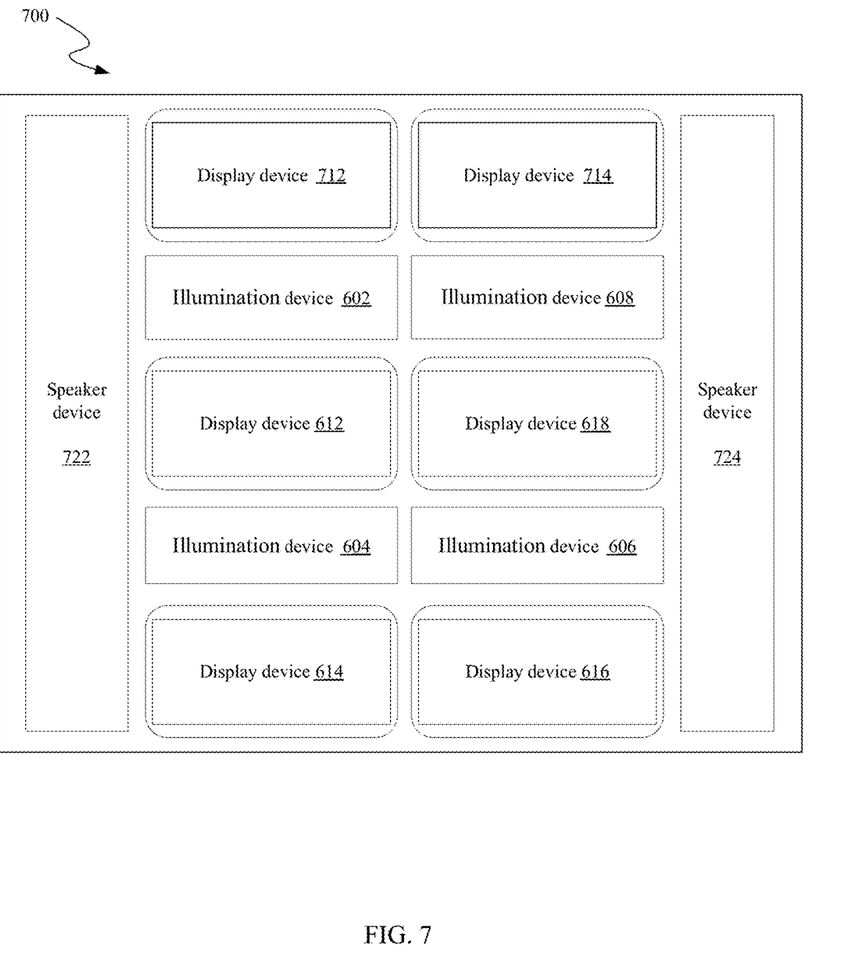
FIG. 7 is a schematic structural diagram of a top portion of the environment simulation structure as illustrated in FIG. 6.
Figure 8:
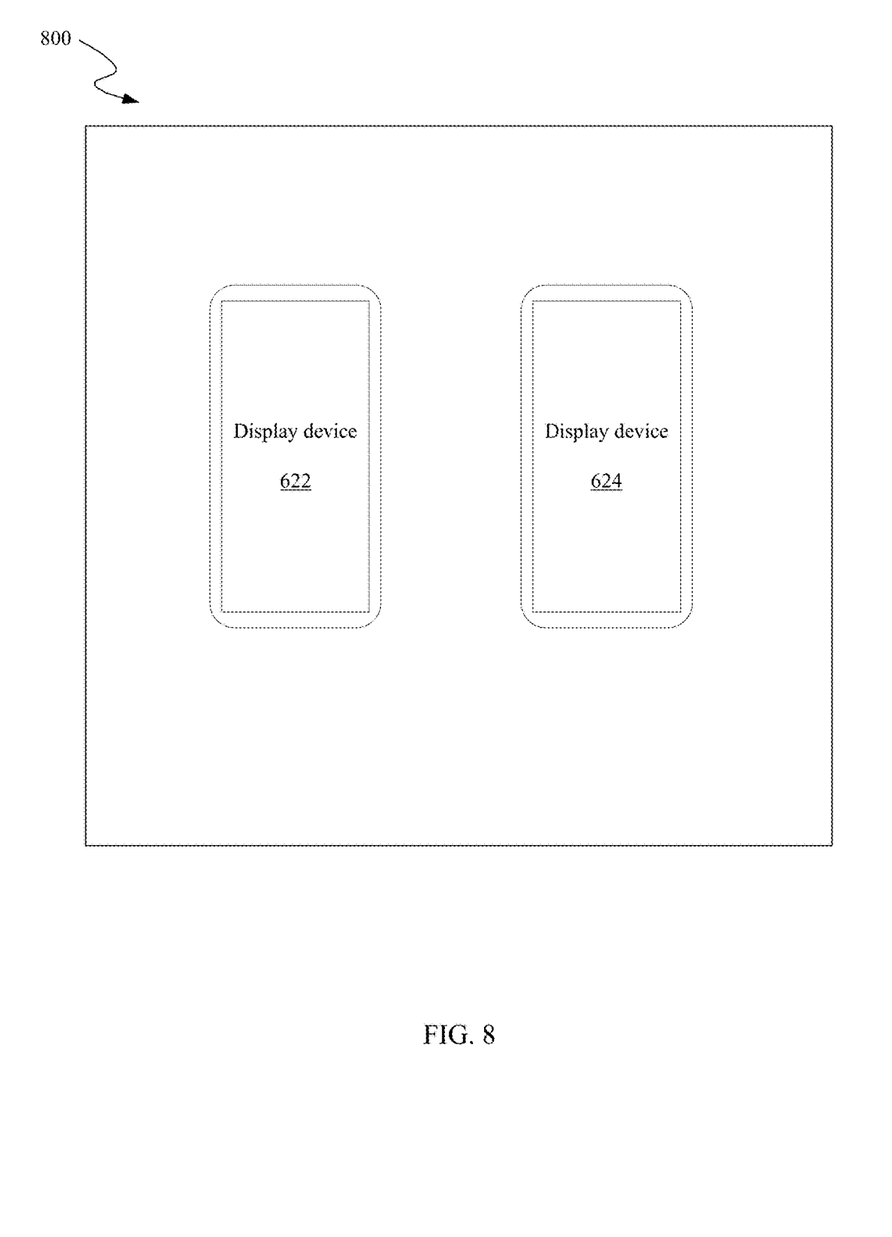
FIG. 8 is a schematic structural diagram of a side wall of the environment simulation structure as illustrated in FIG. 6.

Specifically, with reference to FIG. 7 and FIG. 8, a plurality of illumination devices (for example, four illumination devices 602, 604, 606, and 608) and a plurality of display devices (for example, six display devices 612, 614, 616, 618, 712, and 714) may be disposed on the top portion 700 of the environment simulation structure 206. A plurality of display devices (for example, two display devices 622 and 624) may be disposed on each side wall of the environment simulation structure 206. These display devices may display corresponding images according to patient's preferences, so as to take the patient into a mood of trust and relax during the radiotherapy. For example, the display devices may project video about stars in the space to simulate virtual experience in a space cabin, and may simulate a spectacular scene which is seen from the window of a spacecraft via the display devices disposed on the side wall. When the display devices synchronously play the video about stars in the space, the illumination device may also cooperatively operate, to create a suitable lighting environment. A plurality of speaker devices (for example, two speaker devices 722 and 724) may also be disposed on the top portion 700 of the environment simulation structure 206 to cooperate with the display devices for playing corresponding background music, thereby vividly simulating a desired environment. In addition, the environment simulation structure 206 may further comprises one or a plurality of multimedia players (not illustrated in the drawing), which are coupled to all of the display devices and speaker devices via cables. The multimedia player may be disposed in a concealed location inside the environment simulation structure 206 within a controllable range of a remote controller to facilitate control by the management personnel or patient.

It should be noted that the above display device may be any device, for example a liquid crystal display, capable of providing effect display, and the number of devices to be disposed is not limited in the present invention. On the contrary, a person skilled in the art may make adaptive modifications to the embodiments of the present invention according to practical requirements (for example, site conditions).

More specifically, the above display device (for example, the liquid crystal display) may be securely disposed on the top portion or side wall (for example, the roof or ceiling of the equipment room) via screws. Various shapes of decoration frames (for example, rectangular with arc shapes at the four corners, as illustrated in FIG. 7 and FIG. 8) may also be disposed on the exteriors of the display devices. All of the illumination devices, display devices, speaker devices, and multimedia player(s) (not illustrated in the drawing) may be coupled to each other via cable and may be controlled by the management personnel or patient using the remote controller.

Advantageously, a high quality multimedia player (for example, a high definition DVD) (not illustrated in the drawing) may be used to play the video about stars in the space, and may be coupled to all of the illumination devices, display devices, and speaker devices. In this case, the video about the stars in the space which is played by the multimedia player (not illustrated in the drawing) may be synchronously displayed on each of the display devices, and a desired environment is created under cooperation with the illumination devices and the speaker devices. In this way, the patient would be provided a feeling like in the space, and the equipment room is provided with a space medical cabin, which creates high-tech experience as being in the space medical treatment equipment room, relieves nervousness and anxiety of the patient during the treatment, and improves the effect of diagnosis and treatment. Furthermore, the display devices and the speaker devices may be added to a conventional equipment room, or form a separate closed space in the conventional equipment room. Therefore, the installation of the devices is flexible and cost efficient.

Figure 9A:
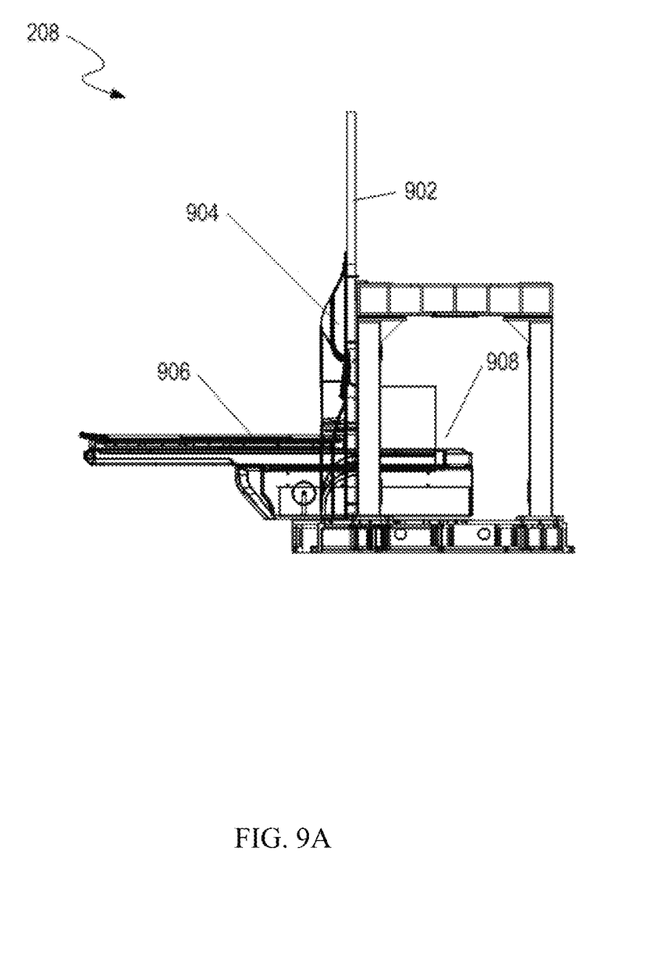
FIG. 9A is a side view of a radiotherapy isolation structure according to an embodiment of the present invention.
Figure 9B:
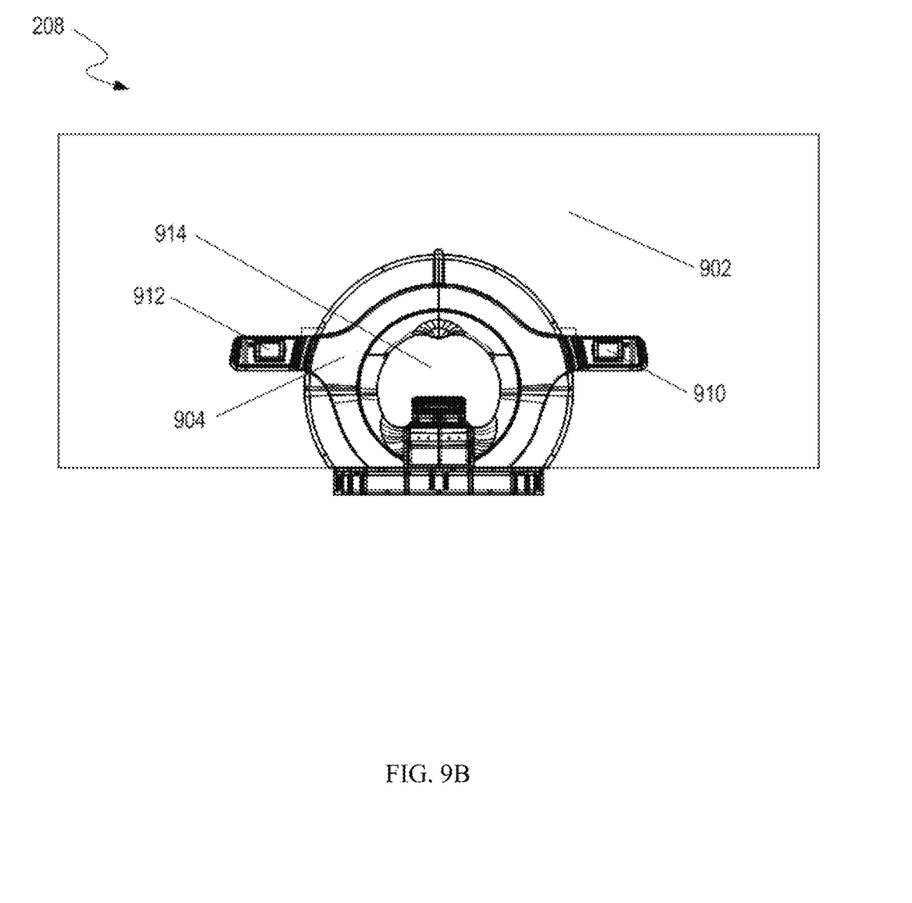
FIG. 9B is a front view of the radiotherapy isolation structure according to an embodiment of the present invention.
Figure 9C:
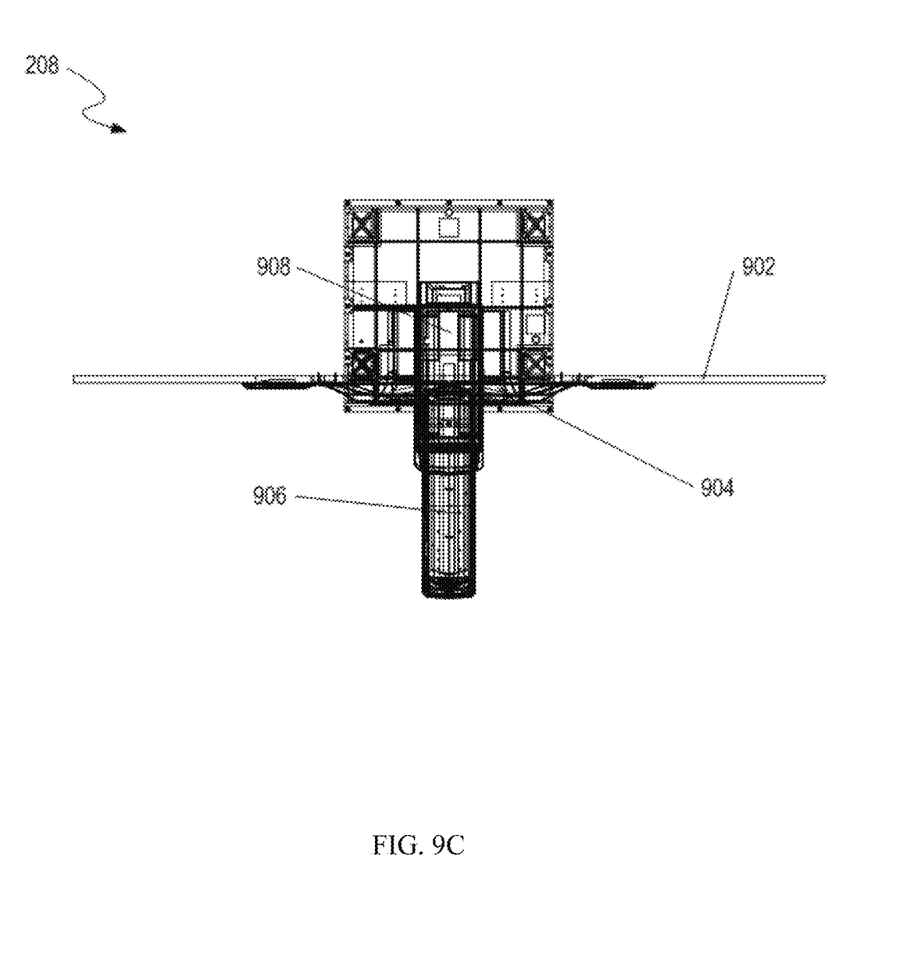
FIG. 9C is a top view of the radiotherapy isolation structure according to an embodiment of the present invention.

The radiotherapy isolation structure 208 is described with reference to FIGS. 9A to 9C. FIGS. 9A to 9C are respectively a side view, a front view and a top view of the radiotherapy isolation structure 208 according to an embodiment of the present invention. The radiotherapy isolation structure 208 comprises an isolation wall 902 and a device model 904. The isolation wall 902 may cause a stereo location region 906 (comprising the treatment couch 210) and a radiotherapy region 908 (comprising the medical equipment 212) to be separated from each other in terms of space, and space sealing is separately performed for the stereo location region 906 and the radiotherapy region 908. Therefore, the isolation wall 902 shades the patient's view and further relieves psychological pressure of the patient before the treatment. The device model 904 is embedded at a reserved installation position on the outer surface of the isolation wall 902. As illustrated in FIG. 9B, a through hole 914 may be preset to communicate the isolation wall 902 and the device model 904. During the radiotherapy, the treatment couch 210 in the stereo location region 906 may reciprocally move via the through hole 914.

Specifically, during the operations, after the patient is positioned in the stereo location region 906, the treatment couch 210 starts moving, and penetrates through the isolation wall 902 via the through hole 914, and then reaches the radiotherapy region 908 for treatment. In addition, in the plane of the isolation structure (for example, on the surface of the device model 904), structures and functions may be extended. For example, an ID reader and liquid crystal touch screens 910 and 912 may be configured according to user requirements. Where necessary, a concealed door (not illustrated in the drawing) may be further disposed on the isolation wall 902 for entry and exit.

More specifically, the isolation wall 902 may be perpendicular to the ground and may be disposed as abutting against an outer end face of the vertical column of the treatment main machine in the radiotherapy region 908, and the isolation wall 902 is coupled to the vertical column of the treatment main machine via screws. The surroundings of the isolation wall 902 are integrally coupled to the base of the equipment room. The device model 904 is embedded at a reserved installation position on the outer surface of the isolation wall 902, and the device model 904 may be coupled to the isolation wall 902 via screws.

A person skilled in the art may understand that although FIGS. 9A to 9C are illustrated using a planar structure as an example, the structure of the isolation wall 902 is merely a concept of an isolation space and is not limited to a planar structure, which may also be a curve structure or a specially-shaped structure.

Advantageously, the isolation structure 902 may separately isolate the stereo location region 906 and the radiotherapy region 908 to form separate and independent sealed spaces. Through design of the isolation structure and the equipment room as a whole, the radiotherapy system is compatible with the environment in the equipment room. Further, the isolation structure may also facilitate extension of the structures and functions behind the isolation wall 902, without causing damages to the model of the treatment main machine.

Disclosed above are merely preferred embodiments of the present invention, and are not intended to define the protection scope of the present invention. Any equivalent variations or replacements made based on the claims of the present invention shall fall within the protection scope of the present invention.

What is claimed is:

1. A medical cabin system, comprising:
   a safety protection system disposed on an entrance of the medical cabin system, wherein the safety protection system is configured to identify a subject based on biometric information regarding the subject and wherein safety protection system comprises a shielding door movable upon identification of the subject;
   an identification system disposed on medical equipment of the medical cabin system or in an enclosed space defined by a stereo location region of the medical cabin system, wherein the identification system is configured to verify whether the subject is permitted to undergo a treatment by retrieving scan-able information carried on an ID card and wherein the scan-able information is associated with the subject;
   an environment simulation system disposed on a top portion and a side wall of the medical cabin system;
   a radiotherapy isolation structure, the radiotherapy isolation structure being a vertical wall that isolates the stereo location region from a radiotherapy region of the medical cabin system;
   one or more other independent walls defining an enclosed space with the vertical wall; and
   wherein the subject is verified for the treatment when the shielding door of the safety protection system has moved at least once to allow the subject to enter the medical cabin system and, after the subject has entered the medical cabin system, the identification system has retrieved the scan-able information carried on the ID card.

2. The medical cabin system according to claim 1, wherein the safety protection system comprises:
   an installation panel disposed on an outer wall surface of the shielding door at the entrance;

a scanning module coupled to a treatment controlling computer of the radiotherapy system and disposed on the installation panel;

a verifying module disposed in the treatment controlling computer;

a control module coupled to the verifying module and a motor unit of the shielding door and disposed in the treatment controlling computer; and an anti-extrusion module disposed on a lateral side of the shielding door and coupled to the control module.

3. The medical cabin system according to claim 2, wherein the anti-extrusion module is coupled to the control module via a cable; and when the anti-extrusion module is subjected to an external resistance, the anti-extrusion module sends a signal to the control module such that the shielding door stops moving and an open door movement program of the shielding door is run to enable the shielding door to be fully opened.

4. The medical cabin system according to claim 1, wherein the identification system comprises:

an installation panel on which an ID reading unit and an information display unit are disposed; and a data processing unit coupled to the ID reading unit and the information display unit and disposed in a treatment controlling computer of the radiotherapy system.

5. The medical cabin system according to claim 4, wherein the ID card comprises a magnetic card, a chip card, a one-dimensional code or a two-dimensional code and the ID reading unit is an ID card reader configured to retrieve the scan-able information carried on the ID card and send the scan-able information to the data processing unit; the data processing unit conducts a search in a local database according to the scan-able information sent by the ID reading unit and outputs corresponding information of a search result to the information display unit for display; the information display unit is an operable touch display configured to display information and, in real time, communicate and interact with the data processing unit.

6. The medical cabin system according to claim 1, wherein the environment simulation system comprises:

a plurality of lighting devices disposed on a top portion or a side wall of the environment simulation system;

a plurality of display devices disposed on the top portion or the side wall of the environment simulation system; and a multimedia player coupled to the plurality of display devices.

7. The medical cabin system according to claim 6, wherein the environment simulation system further comprises a plurality of speaker devices coupled to the multimedia player and configured to cooperate with the plurality of display devices to simulate an environment.

8. The medical cabin system according to claim 6, wherein the multimedia player is disposed in a concealed location inside the environment simulation system and coupled to the plurality of display devices via a cable; and the multimedia player plays a video about stars in the space to simulate virtual experience in a space cabin.

9. The medical cabin system according to claim 1, wherein the radiotherapy isolation structure comprises:

an isolation wall disposed between the stereo location region and the radiotherapy region of the radiotherapy system; and a device model embedded on an outer surface of one side of the isolation wall;

wherein the isolation wall and the device model are each provided with a through hole, and a medical couch disposed in the stereo location region reciprocally moves via the through hole.

10. The medical cabin system according to claim 9, wherein the isolation wall defines independent spaces by enclosing the stereo location region and the radiotherapy region respectively; and the stereo location region is disposed on one side of the isolation wall and the radiotherapy region is disposed on the other side of the isolation wall.

* * * * *